(12) United States Patent
Cumming

(10) Patent No.: US 10,736,732 B2
(45) Date of Patent: Aug. 11, 2020

(54) INTRAOCULAR LENS WITH LONGITUDINALLY RIGID PLATE HAPTIC

(76) Inventor: James Stuart Cumming, Laguna Beach, CA (US)

(*) Notice: Subject to any disclaimer, the term of this patent is extended or adjusted under 35 U.S.C. 154(b) by 736 days.

(21) Appl. No.: 13/017,189

(22) Filed: Jan. 31, 2011

(65) Prior Publication Data

US 2011/0313519 A1  Dec. 22, 2011

Related U.S. Application Data

(60) Provisional application No. 61/398,107, filed on Jun. 21, 2010, provisional application No. 61/398,098, filed on Jun. 21, 2010, provisional application No. 61/398,115, filed on Jun. 21, 2010, provisional application No. 61/398,099, filed on Jun. 21, 2010.

(51) Int. Cl.
*A61F 2/16* (2006.01)
(52) U.S. Cl.
CPC ............... *A61F 2/16* (2013.01); *A61F 2/1624* (2013.01); *A61F 2/1629* (2013.01); *A61F 2002/169* (2015.04); *A61F 2002/1681* (2013.01); *A61F 2002/1682* (2015.04); *A61F 2002/1689* (2013.01); *A61F 2002/16905* (2015.04); *A61F 2220/0091* (2013.01); *A61F 2230/0006* (2013.01); *A61F 2230/0069* (2013.01); *A61F 2250/0018* (2013.01)
(58) Field of Classification Search
CPC .............................. A61F 2/1624; A61F 2/1689
USPC .................................................. 623/6.47–6.49
See application file for complete search history.

(56) References Cited

U.S. PATENT DOCUMENTS

| | | | |
|---|---|---|---|
| 2,834,023 A | 5/1958 | Lieb | |
| 4,073,014 A | 2/1978 | Poler | |
| 4,118,808 A | 10/1978 | Poler | |
| 4,122,556 A | 10/1978 | Poler | |
| 4,159,546 A | 7/1979 | Shearing | |
| 4,168,547 A | 9/1979 | Konstantinov et al. | |
| 4,173,798 A | 11/1979 | Welsh | |
| 4,174,543 A | 11/1979 | Kelman | |
| 4,206,518 A | 6/1980 | Jardon et al. | |
| 4,244,060 A | 1/1981 | Hoffer | |

(Continued)

FOREIGN PATENT DOCUMENTS

| | | |
|---|---|---|
| CA | 2110184 A1 | 12/1992 |
| CH | 681687 | 5/1993 |

(Continued)

OTHER PUBLICATIONS

Dykstra, M., et al. Biological Electron Microscopy: Theory, Techniques, and Troublshooting, 2003, p. 81.

(Continued)

*Primary Examiner* — Leslie Lopez
(74) *Attorney, Agent, or Firm* — Sheppard, Mullin, Richter & Hampton LLP

(57) ABSTRACT

An intraocular lens for insertion into a capsular bag of an eye comprises: an optic; and at least one plate haptic coupled to the optic by one or more flexible connecting members. The plate haptic with projections which are designed to engage the periphery of the capsular bag to center and fixate the intraocular lens within. The haptic includes a longitudinally rigid frame to resist deformation of the haptic.

24 Claims, 1 Drawing Sheet

(56) References Cited

U.S. PATENT DOCUMENTS

| | | |
|---|---|---|
| 4,257,521 A * | 3/1981 | Poler .................... A61F 2/1691 206/205 |
| 4,277,851 A | 7/1981 | Choyce et al. |
| 4,254,509 A | 10/1981 | Tennant |
| 4,298,995 A | 11/1981 | Poler |
| 4,304,012 A | 12/1981 | Richard |
| 4,409,690 A | 10/1983 | Gess |
| 4,409,691 A | 10/1983 | Levy |
| 4,424,597 A | 1/1984 | Schlegel |
| 4,441,217 A | 4/1984 | Cozean, Jr. |
| 4,477,931 A | 10/1984 | Kelman |
| 4,573,998 A | 3/1986 | Mazzocco |
| 4,585,457 A | 4/1986 | Kalb |
| 4,605,411 A | 8/1986 | Fedorov et al. |
| 4,615,702 A * | 10/1986 | Koziol .................... A61L 27/14 623/6.42 |
| 4,629,462 A | 12/1986 | Feaster |
| 4,648,878 A | 3/1987 | Kelman |
| 4,664,665 A | 5/1987 | Reuss et al. |
| 4,664,666 A | 5/1987 | Barrett |
| 4,666,445 A * | 5/1987 | Tillay .................... A61F 2/1613 623/6.18 |
| 4,673,406 A | 6/1987 | Schlegel |
| 4,681,102 A | 7/1987 | Bartell |
| 4,704,123 A | 11/1987 | Smith |
| 4,710,195 A | 12/1987 | Glovinazzo |
| 4,718,904 A | 1/1988 | Thornton |
| 4,731,078 A * | 3/1988 | Stoy .................... A61F 2/1648 623/6.13 |
| 4,737,322 A | 4/1988 | Bruns et al. |
| 4,738,680 A | 4/1988 | Herman |
| 4,743,254 A | 5/1988 | Davenport |
| 4,753,655 A | 6/1988 | Hecht |
| 4,759,761 A | 7/1988 | Portnoy |
| 4,763,650 A | 8/1988 | Hauser |
| 4,765,329 A | 8/1988 | Cumming et al. |
| 4,769,033 A | 9/1988 | Nordan |
| 4,769,035 A | 9/1988 | Kelman |
| 4,772,283 A | 9/1988 | White |
| 4,778,463 A | 10/1988 | Hetland |
| 4,781,719 A | 11/1988 | Kelman |
| 4,787,904 A * | 11/1988 | Severin ................. A61F 2/1613 623/6.56 |
| 4,790,847 A | 12/1988 | Woods |
| 4,793,344 A | 12/1988 | Cumming et al. |
| 4,813,955 A | 3/1989 | Achatz et al. |
| 4,816,030 A | 3/1989 | Robinson |
| 4,840,627 A | 6/1989 | Blumenthal |
| 4,842,599 A | 6/1989 | Bronstein |
| 4,842,601 A | 6/1989 | Smith |
| 4,846,833 A | 7/1989 | Cumming |
| 4,862,885 A | 9/1989 | Cumming |
| 4,865,601 A | 9/1989 | Caldwell et al. |
| 4,868,251 A | 9/1989 | Reich et al. |
| 4,880,427 A | 11/1989 | Anis |
| 4,888,012 A | 12/1989 | Horn et al. |
| 4,892,543 A | 1/1990 | Turley |
| 4,919,130 A | 4/1990 | Stoy et al. |
| 4,932,966 A | 6/1990 | Christie et al. |
| 4,932,968 A | 6/1990 | Caldwell et al. |
| 4,932,970 A | 6/1990 | Portney |
| 4,936,850 A | 6/1990 | Barrett |
| 4,963,148 A | 10/1990 | Sulc et al. |
| 4,969,897 A | 11/1990 | Kalb |
| 4,976,716 A | 12/1990 | Cumming |
| 4,978,354 A | 12/1990 | Van Gent |
| 4,994,082 A | 2/1991 | Richards et al. |
| 5,047,051 A | 9/1991 | Cumming |
| 5,066,297 A | 11/1991 | Cumming |
| 5,078,742 A | 1/1992 | Dahan |
| 5,089,022 A | 2/1992 | Koester et al. |
| 5,139,518 A | 8/1992 | White |
| 5,141,507 A | 8/1992 | Paraekh |
| 5,152,788 A | 10/1992 | Isaacson et al. |
| 5,152,789 A | 10/1992 | Willis |
| 5,171,319 A | 12/1992 | Keates et al. |
| 5,171,320 A | 12/1992 | Nishi |
| 5,180,390 A | 1/1993 | Drews |
| 5,217,490 A | 6/1993 | Sayano et al. |
| 5,275,604 A | 1/1994 | Rheinish et al. |
| 5,275,623 A | 1/1994 | Sarfarazi |
| 5,275,624 A | 1/1994 | Hara et al. |
| 5,290,310 A | 3/1994 | Makower et al. |
| 5,304,182 A | 4/1994 | Rheinish et al. |
| 5,324,306 A | 6/1994 | Makower et al. |
| 5,326,347 A | 7/1994 | Cumming |
| 5,366,502 A | 11/1994 | Patel |
| 5,376,115 A | 12/1994 | Jansen |
| 5,425,734 A | 6/1995 | Blake |
| 5,443,506 A | 8/1995 | Garabet |
| 5,474,562 A | 12/1995 | Orchowski et al. |
| 5,476,514 A | 12/1995 | Cumming |
| 5,489,302 A | 2/1996 | Skottun |
| 5,496,366 A | 3/1996 | Cumming |
| 5,522,891 A | 6/1996 | Klaas |
| 5,562,731 A | 10/1996 | Cumming |
| 5,578,042 A | 11/1996 | Cumming |
| 5,578,078 A | 11/1996 | Nakajima et al. |
| 5,607,472 A | 3/1997 | Thompson |
| 5,611,968 A | 3/1997 | Grisoni et al. |
| 5,647,865 A | 7/1997 | Swinger |
| 5,674,282 A | 10/1997 | Cumming |
| 5,686,414 A | 11/1997 | Scannon |
| 5,699,142 A | 12/1997 | Lee et al. |
| 5,716,403 A | 2/1998 | Tran |
| 5,762,836 A * | 6/1998 | Bos .................... A61F 2/1616 264/1.7 |
| 5,800,532 A | 9/1998 | Lieberman |
| 5,837,156 A | 11/1998 | Cumming |
| 5,843,187 A | 12/1998 | Bayers |
| 5,873,879 A | 2/1999 | Figueroa et al. |
| 5,919,230 A * | 7/1999 | Sambursky ........... A61F 2/1616 623/6.44 |
| 5,944,725 A | 8/1999 | Cicenas et al. |
| 5,968,094 A | 10/1999 | Werblin et al. |
| 5,984,914 A | 11/1999 | Cumming |
| 6,007,579 A | 12/1999 | Lipshitz et al. |
| 6,013,101 A | 1/2000 | Israel |
| 6,015,435 A | 1/2000 | Valunin et al. |
| 6,027,531 A | 2/2000 | Tassignon |
| 6,051,024 A | 4/2000 | Cumming |
| 6,066,171 A | 5/2000 | Lipshitz et al. |
| 6,066,172 A | 5/2000 | Huo et al. |
| 6,113,633 A | 9/2000 | Portney |
| 6,129,760 A | 10/2000 | Fedorov et al. |
| 6,161,544 A | 12/2000 | DeVore |
| 6,164,282 A | 12/2000 | Gwon et al. |
| 6,176,878 B1 | 1/2001 | Gwon et al. |
| 6,179,870 B1 | 1/2001 | Sourdille et al. |
| 6,193,750 B1 | 2/2001 | Cumming |
| 6,197,058 B1 | 3/2001 | Portney |
| 6,197,059 B1 * | 3/2001 | Cumming .............. A61F 2/1629 623/6.39 |
| 6,217,612 B1 | 4/2001 | Woods |
| 6,299,641 B1 | 10/2001 | Woods |
| 6,302,911 B1 | 10/2001 | Hanna |
| 6,322,589 B1 | 11/2001 | Cumming |
| 6,342,073 B1 | 1/2002 | Cumming et al. |
| 6,387,126 B1 | 5/2002 | Cumming |
| 6,391,056 B2 | 5/2002 | Cumming |
| 6,406,494 B1 | 6/2002 | Laguette et al. |
| 6,409,763 B1 | 6/2002 | Brady |
| 6,413,276 B1 | 7/2002 | Werblin |
| 6,413,277 B1 * | 7/2002 | Neuhann ................ A61F 2/1694 623/6.11 |
| 6,419,697 B1 | 7/2002 | Kelman |
| 6,423,094 B1 | 7/2002 | Sarfarazi |
| 6,443,985 B1 | 9/2002 | Woods |
| 6,451,056 B1 | 9/2002 | Cumming |
| 6,461,384 B1 | 10/2002 | Hoffmann et al. |
| 6,488,708 B2 | 12/2002 | Sarfarazi |
| 6,494,911 B2 | 12/2002 | Cumming |
| 6,497,708 B1 | 12/2002 | Cumming |

(56) References Cited

U.S. PATENT DOCUMENTS

| | | | |
|---|---|---|---|
| 6,503,275 B1 | 1/2003 | Cumming | |
| 6,503,276 B2 | 1/2003 | Lang et al. | |
| 6,517,577 B1 | 2/2003 | Callahan et al. | |
| 6,524,340 B2 | 2/2003 | Israel | |
| 6,540,353 B1 | 4/2003 | Dunn | |
| 6,558,420 B2 | 5/2003 | Green | |
| 6,613,343 B2 | 9/2003 | Dillingham et al. | |
| 6,616,691 B1 | 9/2003 | Tran | |
| 6,616,692 B1 | 9/2003 | Glick et al. | |
| 6,638,305 B2 | 10/2003 | Laguette | |
| 6,638,306 B2 | 10/2003 | Cumming | |
| 6,645,245 B1 | 11/2003 | Preussner | |
| 6,660,035 B1 | 12/2003 | Lang et al. | |
| 6,660,036 B2 | 12/2003 | Cumming | |
| 6,685,741 B2 | 2/2004 | Landreville et al. | |
| 6,695,881 B2 | 2/2004 | Peng et al. | |
| 6,749,634 B2 | 6/2004 | Hanna | |
| 6,767,363 B1 | 7/2004 | Bandhauer et al. | |
| 6,849,091 B1 * | 2/2005 | Cumming | A61F 2/1629 623/6.18 |
| 6,858,040 B2 | 2/2005 | Nguyen et al. | |
| 6,881,225 B2 | 4/2005 | Okada | |
| 6,884,263 B2 | 4/2005 | Valyunin | |
| 6,921,416 B2 | 7/2005 | Khoury | |
| 6,926,736 B2 | 8/2005 | Peng | |
| 6,932,839 B1 | 8/2005 | Kamerling et al. | |
| 6,942,695 B1 * | 9/2005 | Chapoy | A61F 2/1613 623/6.5 |
| 6,969,403 B2 | 11/2005 | Peng | |
| 6,972,033 B2 | 12/2005 | McNicholas | |
| 7,018,409 B2 | 3/2006 | Glick | |
| 7,025,783 B2 | 4/2006 | Brady | |
| 7,037,338 B2 | 5/2006 | Nagamoto | |
| 7,048,760 B2 | 5/2006 | Cumming | |
| 7,097,660 B2 | 8/2006 | Portney | |
| 7,125,422 B2 | 10/2006 | Woods et al. | |
| 7,150,759 B2 | 12/2006 | Paul et al. | |
| 7,150,760 B2 | 12/2006 | Zhang | |
| 7,229,475 B2 | 6/2007 | Glazier | |
| 7,229,476 B2 | 6/2007 | Azar | |
| 7,300,464 B2 | 11/2007 | Tran | |
| 7,326,246 B2 | 2/2008 | Brady | |
| 7,341,599 B1 | 3/2008 | Peyman | |
| 7,435,258 B2 | 10/2008 | Blake | |
| 7,435,259 B2 | 10/2008 | Cumming | |
| 7,553,327 B2 | 6/2009 | Cumming | |
| 7,662,180 B2 | 2/2010 | Paul et al. | |
| 7,763,070 B2 | 7/2010 | Cumming | |
| 7,837,730 B2 | 11/2010 | Cumming | |
| 7,981,155 B2 | 7/2011 | Cumming | |
| 7,985,253 B2 | 7/2011 | Cumming | |
| 8,038,711 B2 | 10/2011 | Clarke | |
| 8,080,056 B2 | 12/2011 | Cumming | |
| 8,100,965 B2 | 1/2012 | Cumming et al. | |
| 8,109,998 B2 | 2/2012 | Cumming | |
| 8,163,015 B2 | 4/2012 | Cumming | |
| 8,216,308 B2 | 7/2012 | Blake et al. | |
| 8,388,608 B1 | 3/2013 | Kaluzna | |
| 8,523,942 B2 | 9/2013 | Cumming | |
| 8,734,512 B2 | 5/2014 | Cumming | |
| 8,764,823 B2 | 7/2014 | Cumming | |
| 9,034,036 B2 | 5/2015 | Cumming | |
| 2001/0001836 A1 | 5/2001 | Cumming | |
| 2002/0120329 A1 | 8/2002 | Lang et al. | |
| 2002/0138140 A1 | 9/2002 | Hanna | |
| 2003/0060881 A1 | 3/2003 | Glick et al. | |
| 2003/0078658 A1 | 4/2003 | Zadno-Azizi | |
| 2003/0097177 A1 | 5/2003 | Tran | |
| 2003/0109925 A1 | 6/2003 | Ghazizadeh et al. | |
| 2003/0135272 A1 * | 7/2003 | Brady et al. | 623/6.37 |
| 2003/0142269 A1 | 7/2003 | Cumming | |
| 2003/0171808 A1 | 9/2003 | Phillips | |
| 2003/0171809 A1 | 9/2003 | Phillips | |
| 2003/0187505 A1 | 10/2003 | Liao | |
| 2003/0199977 A1 | 10/2003 | Cumming | |
| 2003/0204257 A1 * | 10/2003 | Southard | 623/6.46 |
| 2004/0002757 A1 | 1/2004 | Lai et al. | |
| 2004/0015236 A1 | 1/2004 | Sarfarazi | |
| 2004/0082993 A1 | 4/2004 | Woods | |
| 2004/0082994 A1 | 4/2004 | Woods et al. | |
| 2004/0111151 A1 * | 6/2004 | Paul | A61F 2/1613 623/6.37 |
| 2004/0111152 A1 | 6/2004 | Kelman | |
| 2004/0148023 A1 | 7/2004 | Shu | |
| 2004/0215207 A1 | 10/2004 | Cumming | |
| 2004/0215340 A1 * | 10/2004 | Messner | A61F 2/1613 623/6.37 |
| 2004/0220666 A1 | 11/2004 | Cumming | |
| 2004/0243232 A1 | 12/2004 | Cumming | |
| 2004/0249456 A1 | 12/2004 | Cumming | |
| 2005/0021140 A1 | 1/2005 | Liao | |
| 2005/0027354 A1 | 2/2005 | Brady et al. | |
| 2005/0075732 A1 | 4/2005 | Israel | |
| 2005/0096741 A1 | 5/2005 | Cumming | |
| 2005/0107875 A1 * | 5/2005 | Cumming | A61F 2/1613 623/6.37 |
| 2005/0125058 A1 * | 6/2005 | Cumming | A61F 2/1613 623/6.37 |
| 2005/0137703 A1 | 6/2005 | Chen | |
| 2005/0149184 A1 * | 7/2005 | Bogaert | A61F 2/1602 623/6.14 |
| 2005/0267576 A1 | 12/2005 | Cumming | |
| 2005/0288784 A1 | 12/2005 | Peyman | |
| 2006/0064077 A1 | 3/2006 | Peyman | |
| 2006/0064162 A1 | 3/2006 | Klima | |
| 2006/0100704 A1 | 5/2006 | Blake et al. | |
| 2006/0111776 A1 | 5/2006 | Glick et al. | |
| 2006/0116764 A1 | 6/2006 | Simpson | |
| 2006/0149369 A1 | 7/2006 | Cumming et al. | |
| 2006/0259140 A1 * | 11/2006 | Dell | A61F 2/1629 623/6.38 |
| 2007/0005136 A1 * | 1/2007 | Richardson | A61F 2/1629 623/6.34 |
| 2007/0012832 A1 | 1/2007 | Ottens et al. | |
| 2007/0032867 A1 | 2/2007 | Cumming | |
| 2007/0129800 A1 | 6/2007 | Cumming | |
| 2007/0129803 A1 | 6/2007 | Cumming et al. | |
| 2007/0135915 A1 * | 6/2007 | Klima | A61F 2/1629 623/6.37 |
| 2007/0142908 A1 | 6/2007 | Xu | |
| 2007/0198084 A1 | 8/2007 | Cumming et al. | |
| 2007/0244472 A1 | 10/2007 | Kuhn et al. | |
| 2008/0027538 A1 | 1/2008 | Cumming | |
| 2008/0027539 A1 | 1/2008 | Cumming | |
| 2008/0027540 A1 | 1/2008 | Cumming | |
| 2008/0046077 A1 | 2/2008 | Cumming | |
| 2008/0086208 A1 | 4/2008 | Nordan | |
| 2008/0154362 A1 | 6/2008 | Cumming | |
| 2008/0188930 A1 * | 8/2008 | Mentak | A61F 2/1627 623/6.13 |
| 2008/0281415 A1 | 11/2008 | Cumming | |
| 2008/0281416 A1 | 11/2008 | Cumming | |
| 2008/0288066 A1 | 11/2008 | Cumming | |
| 2008/0294254 A1 * | 11/2008 | Cumming | A61F 2/1613 623/6.37 |
| 2008/0319545 A1 | 12/2008 | Cumming | |
| 2009/0005866 A1 | 1/2009 | Cumming | |
| 2009/0234449 A1 | 9/2009 | De Juan, Jr. et al. | |
| 2009/0248154 A1 | 10/2009 | Dell | |
| 2010/0004742 A1 | 1/2010 | Cumming | |
| 2010/0057202 A1 | 3/2010 | Bogaert | |
| 2011/0313524 A1 | 12/2011 | Cumming | |
| 2011/0313525 A1 | 12/2011 | Cumming | |
| 2012/0296424 A1 | 11/2012 | Betser | |
| 2012/0296425 A1 * | 11/2012 | Cumming | A61F 2/1627 623/6.46 |
| 2012/0310344 A1 * | 12/2012 | Cumming | A61F 2/1624 623/6.44 |
| 2013/0073039 A1 | 3/2013 | Mirlay | |
| 2013/0231742 A1 | 9/2013 | Deacon et al. | |
| 2014/0088699 A1 | 3/2014 | Cumming | |
| 2014/0094909 A1 | 4/2014 | Cumming | |
| 2014/0155871 A1 | 6/2014 | Cumming | |

(56) References Cited

U.S. PATENT DOCUMENTS

| | | |
|---|---|---|
| 2014/0172093 A1 | 6/2014 | Cumming |
| 2015/0012088 A1 | 1/2015 | Cumming |
| 2015/0073550 A1 | 3/2015 | Cumming |
| 2015/0088254 A1 | 3/2015 | Cumming |

FOREIGN PATENT DOCUMENTS

| | | |
|---|---|---|
| DE | 3626869 | 2/1988 |
| FR | 2728458 | 6/1996 |
| FR | 2728459 | 6/1996 |
| FR | 2734472 | 11/1996 |
| FR | 2765797 | 1/1999 |
| FR | 2991572 | 12/2013 |
| GB | 2171912 | 9/1986 |
| GB | 2226246 | 6/1990 |
| JP | 2003-190193 | 7/2003 |
| SU | 1123685 | 11/1984 |
| WO | WO 93/05733 | 4/1993 |
| WO | WO 01/19288 | 3/2001 |
| WO | WO 01/19289 | 3/2001 |
| WO | WO 03/017873 | 3/2003 |
| WO | WO 2007/037180 | 4/2007 |
| WO | 2008/150890 A1 | 12/2008 |
| WO | WO 2009/048656 | 4/2009 |
| WO | WO 2009/086511 | 7/2009 |

OTHER PUBLICATIONS

Final Office Action for U.S. Appl. No. 13/092,359 dated Mar. 5, 2013 in 11 pages.
Final Office Action for U.S. Appl. No. 13/111,599 dated May 2, 2013 in 10 pages.
Final Office Action for U.S. Appl. No. 13/155,327 dated Dec. 10, 2012 in 10 pages.
Final Office Action for U.S. Appl. No. 13/953,605 dated Sep. 25, 2014 in 17 pages.
International Search Report and Written Opinion for PCT/US13/61452 dated Feb. 24, 2014 in 11 pages.
Office Action for U.S. Appl. No. 13/092,359 dated Oct. 25, 2012 in 10 pages.
Office Action for U.S. Appl. No. 13/092,359 dated Sep. 8, 2014 in 15 pages.
Office Action for U.S. Appl. No. 13/111,599 dated Jan. 2, 2013 in 11 pages.
Office Action for U.S. Appl. No. 13/111,599 dated Sep. 5, 2014 in 13 pages.
Office Action for U.S. Appl. No. 13/155,327 dated Jul. 20, 2012 in 7 pages.
Office Action for U.S. Appl. No. 13/155,327 dated Apr. 26, 2013 in 7 pages.
Office Action for U.S. Appl. No. 13/953,605 dated May 20, 2014 in 9 pages.
Office Action for U.S. Appl. No. 13/891,088 dated Aug. 13, 2014 in 25 pages.
Office Action for U.S. Appl. No. 13/910,076 dated Nov. 7, 2014 in 12 pages.
Office Action for U.S. Appl. No. 14/143,162 dated Aug. 4, 2014 in 18 pages.
Office Action for U.S. Appl. No. 14/257,933 dated Oct. 31, 2014 in 9 pages.
Response to Office Action for U.S. Appl. No. 13/092,359 dated Jan. 31, 2013 in 8 pages.
Response to Final Office Action for U.S. Appl. No. 13/092,359 dated Jul. 29, 2013 in 7 pages.
Response to Office Action for U.S. Appl. No. 13/111,599 dated Apr. 9, 2013 in 6 pages.
Response to Office Action for U.S. Appl. No. 13/111,599 dated Jul. 30, 2013 in 6 pages.
Response to Office Action for U.S. Appl. No. 13/155,327 dated Oct. 26, 2012 in 5 pages.
Response to Office Action for U.S. Appl. No. 13/155,327 dated Apr. 10, 2013 in 5 pages.
Response to Office Action for U.S. Appl. No. 13/155,327 dated Jul. 25, 2013 in 5 pages.
Response to Office Action for U.S. Appl. No. 13/953,605 dated Aug. 19, 2014 in 7 pages.
Response to Office Action for U.S. Appl. No. 13/891,088 dated Dec. 15, 2014 in 8 pages.
Final Office Action for U.S. Appl. No. 13/092,359 dated Feb. 6, 2015 in 21 pages.
Final Office Action for U.S. Appl. No. 13/111,599 dated Feb. 6, 2015 in 21 pages.
Final Office Action for U.S. Appl. No. 14/143,612 dated Mar. 20, 2015 in 14 pages.
Final Office Action for U.S. Appl. No. 14/257,933 dated Mar. 19, 2015 in 23 pages.
International Search Report and Written Opinion for PCT/US2014/057037 dated Jan. 20, 2015 in 12 pages.
Office Action for U.S. Appl. No. 14/270,166 dated Mar. 3, 2015 in 19 pages.
Office Action for U.S. Appl. No. 14/274,352 dated Feb. 12, 2015 in 10 pages.
Office Action for U.S. Appl. No. 14/035,813 dated Mar. 26, 2015 in 16 pages.
Response to Final Office Action for U.S. Appl. No. 13/092,359 dated Jan. 8, 2015 in 9 pages.
Response to Office Action for U.S. Appl. No. 13/111,599 dated Jan. 6, 2015 in 13 pages.
Response to Final Office Action for U.S. Appl. No. 13/953,605 dated Dec. 18, 2014 in 12 pages.
Response to Office Action for U.S. Appl. No. 13/910,076 dated Feb. 9, 2015 in 10 pages.
Response to Office Action for U.S. Appl. No. 14/143,612 dated Jan. 5, 2015 in 8 pages.
Response to Office Action for U.S. Appl. No. 14/257,933 dated Feb. 2, 2015 in 10 pages.
Final Office Action for U.S. Appl. No. 14/274,352 dated Jun. 8, 2015 in 27 pages.
Office Action for U.S. Appl. No. 13/092,359 dated Jun. 5, 2015 in 11 pages.
Office Action for U.S. Appl. No. 13/910,076 dated Apr. 10, 2015 in 26 pages.
Office Action for U.S. Appl. No. 14/035,821 dated Apr. 13, 2015 in 33 pages.
Response to Final Office Action for U.S. Appl. No. 13/092,359 dated May 6, 2015 in 9 pages.
Response to Office Action for U.S. Appl. No. 13/111,599 dated Jun. 8, 2015 in 13 pages.
Response to Office Action for U.S. Appl. No. 14/274,352 dated May 12, 2015 in 10 pages.
Internet Archive Wayback Machine; Crystalens—Is Crystalens right for you?; downloaded from http://web.archive.org/web/20141025080709/http://crystalens.com/en-us/iscrystalensrightforyou.aspx (Archived Oct. 25, 2014; printed on Aug. 12, 2015).
Davison, J.A., Chapter 11: Intraocular Lenses, Duane's Clinical Ophthalmology on CD-ROM, Lippincott Williams & Wilkins, 2005, vol. 6, pp. 1-46.

* cited by examiner

INTRAOCULAR LENS WITH LONGITUDINALLY RIGID PLATE HAPTIC

CROSS-REFERENCE TO RELATED APPLICATIONS

Pursuant to 35 U.S.C. § 120, this application claims the benefit of the filing of U.S. Provisional Patent Application Nos. 61/398,107, filed on Jun. 21, 2010, 61/398,098 filed on Jun. 21, 2010, 61/398,115, filed on Jun. 21, 2010 and 61/398,099, filed Jun. 21, 2010, the contents of which are incorporated by reference herein.

BACKGROUND OF THE INVENTION

Accommodating Intraocular Lenses were developed in the early 1900's and have been sold in Europe for the last ten years and later in the U.S. They function by means of forward movement of the optic upon constriction of the ciliary muscle which increases the pressure in the posterior part of the eye with a simultaneous decrease in pressure in the front part of the eye pressure. The reverse pressure changes take place upon relaxation of the ciliary muscle, which results in the backwards movement of the lens for distance vision. The forward movement of the lens optic enables the patient implanted with the lens to automatically change their vision from distance to see at intermediate and near.

The currently marketed accommodating plate haptic intraocular lenses provide excellent distance and intermediate vision but sometimes require weak, +1.00, reading glasses for prolonged reading, for seeing small print, or reading in dim lighting conditions. The embodiments relating to the present invention presented herein are designed to substantially reduce the need for any reading glasses It is important for intraocular lenses to have a consistent location along the axis of the eye to provide good uncorrected distance vision and to center in the middle of the vertical meridian of the eye. Without excellent uncorrected distance vision there is no point in implanting an accommodating lens whose function is to enable patients to be without glasses. With the advent of the new premium lenses, not only are the above requirements important but also the vision is likely to be better if the lens after implantation and centration, is without any tilt which can reduce the quality of vision particularly if the lens optic has a toric component or is a multifocal.

The word "haptic" has been used to describe an attachment to intraocular lenses. The original intraocular lens consisted of a single optic. These single optic lenses, without any attachments, were first implanted in London by Harold Ridley in 1949. These lenses frequently de-centered and it was discovered that there was a need to center and fixate the lens optic in the vertical meridian of the eye.

The first attachments to the optic were called "haptics". They consisted of multiple flexible loops of various designs, J loops, C loops, closed loops and flexible radial arms.

Later, these loops which became commonly referred to as "haptics" were replaced in some lens designs with plates, called "plate haptics". It is necessary to fixate and center the plate haptics within the capsular bag and so loops or fingers are extended from the distal lateral ends of the plate haptics. These can be of the same material as the plate or integrally molded into the plate lens design during manufacturing, and can be made of polyimide, prolene, PMMA or titanium.

When the accommodating lens plate haptic is fibrosed into the capsular bag of an eye after cataract surgery, sometimes several weeks or months following the surgery, a complication can occur. The lens can deform to a "Z" dislocated shape. This occurs when there is little sandwiching of the distal tip of the plate haptics between the remaining anterior and the posterior walls of the capsular bag.

The current accommodating lenses utilize an oblong lens body design having plate haptics connected to the lens optics by a single transverse hinge across the plate haptic. This promotes accommodation by allowing the optic to move forwards and backwards relative to the outer, or distal, ends of the plates. Such accommodating lenses are found in U.S. Pat. Nos. 5,476,514 and 5,496,366, both to Cumming, the disclosures of which are herein incorporated by reference. However, these designs do not permit adequate movement of the optic to a change in vitreous cavity pressure to allow many patients to read comfortably at near without glasses.

In order to increase the movement of the optic to respond to the increase in vitreous cavity pressure that occurs during constriction of the ciliary muscle, the transverse hinge may be weakened by elongating the hinge base or reducing the width of the hinge. However, elongating the hinge base would destabilize the lens optic, and making the hinge narrower would make it prone to tilting.

BRIEF SUMMARY PREFERRED EMBODIMENTS

An intraocular lens design according to an embodiment of the present invention is described that overcomes the deficiencies of present designs noted above.

A flat, longitudinal intraocular lens is provided, having distinct separate plate haptics that are rigid longitudinally, and that extend to partially surround the optic. The flat plate haptics may have a groove or hinge across the width of its proximal ends adjacent to the optic. This hinge may be weakened by having at least two separate spaced apart narrow hinges on each edge of the plate haptics, thereby, reducing the overall width of the hinge. This plural strap design stabilizes the lens optic while reducing the resistance of the optic to a change in vitreous cavity pressure, thereby, allowing more movement of the optic along the axis of the eye. Further stabilization is achieved by making the haptics as wide, or wider, than the optic and extending the lateral proximal ends of the plate haptics to partially surround the optic. The plate haptics may be made rigid longitudinally by incorporating into the length of the haptics a rigid frame structure.

Thus, an intraocular lens according to the present invention may stabilize the solid, single, flexible lens optic, prevent tilt, provide more movement of the optic for better near vision and center and fixate the lens in the capsular bag with the finger-like flexible loops at the distal ends of the plates.

Other features and advantages of the present invention will become apparent from the following more detailed description, taken in conjunction with the accompanying drawings, which illustrate, by way of example, the principles of the presently described apparatus and method of its use.

BRIEF DESCRIPTION OF THE SEVERAL VIEWS OF THE DRAWING(S)

Illustrated in the accompanying drawing(s) is at least preferred embodiment of the present invention In such drawing(s):

DETAILED DESCRIPTION OF THE PREFERRED EMBODIMENTS

The above described drawing figures illustrate the described invention and method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Figure 1:
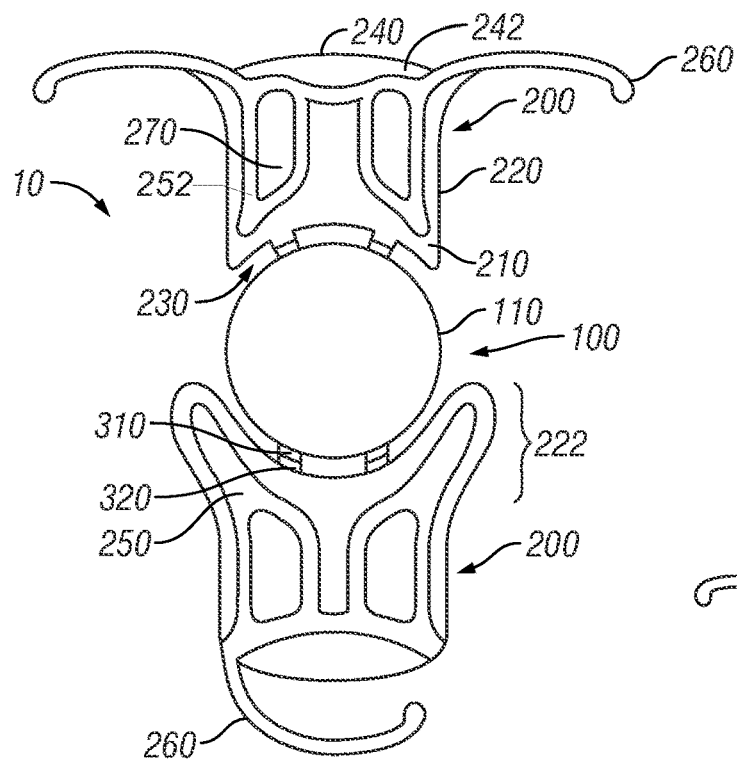
FIG. 1 illustrates a top view of an intraocular lens according to an embodiment of the present invention.
Figure 3:
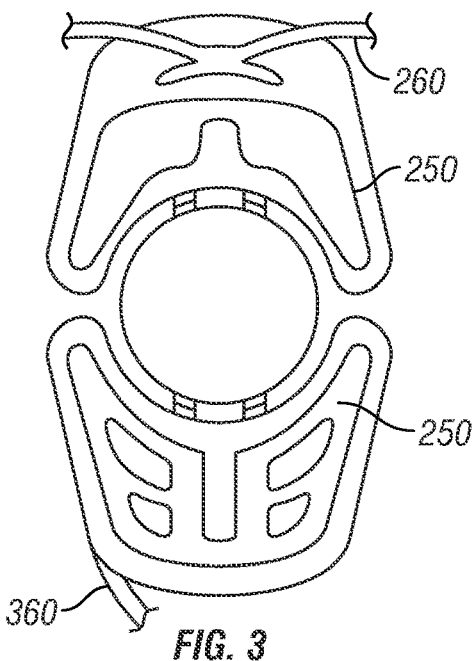
FIG. 3 illustrates a top view of exemplary frames according to an embodiment of the present invention.

As illustrated in FIGS. 1 and 3, an intraocular accommodating lens 10 for insertion into an eye having a ciliary body, comprises: a lens optic 100 having a longitudinal axis and a normal axis perpendicular thereto, and one or more plate haptics 200 coupled to the optic via at least one connecting member 300.

The lens optic is preferably constructed of a flexible optical material such as silicone, hydrogel, acrylic material, but may be made of any similar material. Additionally, the lens optic is preferably shaped so as to be biconvex, refractive, diffractive, plano-convex, Fresnell, spheric, aspheric, toric or multifocal.

In a preferred embodiment, at least two plate haptics 200 are longitudinally coupled to opposing ends of the lens optic 100. As illustrated in FIGS. 1 and 3, each plate haptic 200 may comprise: a frame 250, a body 210, and at least one projection 260.

Turning now to FIG. 1, the body of the haptic comprises at least one lateral end 220 a proximal end 230, a distal end 240 and a plate 270. The haptic body is preferably rigid longitudinally, and is preferably made of silicone, hydrogel, acrylic, or similar material. In one embodiment, the plate haptic body may be of substantially the same width as the lens optic. Thus, the lateral ends may extend substantially parallel to each other and substantially tangential to the lens optic. In another embodiment, the lateral and proximal ends of the plate haptics may comprise a proximal flange, or paddle, 222, as shown in FIG. 3, that partially surrounds the optic and makes the haptic at least as wide as the optic. In one embodiment, the haptic is wider than the optic. Such construction offers increased stabilization of the optic and the plate. Preferably, the width of the haptic is approximately between 3.0 and 7.0 mm. Ideally the width of the haptic is between 4.50 and 6.00 mm. Preferably the haptic thickness is between 0.20 to 0.75 mm. The optic diameter preferably varies from 4.5-7.0 mm, and in one embodiment is approximately 5.0 mm.

As shown in FIG. 1, the plate haptics may further compose at least one substantially flexible projection 260 extending substantially from the distal end. The projection may comprise: an open loop, a closed loop, a tangential extension, a notch or indentation in the distal end 240, or a lateral extension of the distal end, or any combination of the preceding or other geometries known in the art. The flexible projections or fingers may be of the same material as the plate haptic and/or the lens optic, or may be polyimide, prolene, polymethylmethanylate (PMMA), titanium or similar material. In one embodiment, the projection comprises a homogenous integral part of the plate haptic body. In another embodiment, the projection comprises a distinct unit set into the plate haptic during molding. Preferably, the projections measure from 2.0 to 4.0 mm in length extending from the distal end of the haptic body and are flexible extending to a transverse diameter that exceeds the diameter of the capsular bag.

As illustrated in FIG. 1, the plate haptic may further compose a frame 250 operable to strengthen the plate haptic and substantially reduce the flexibility of the plate haptic in at least one direction. In one embodiment, the frame comprises a plurality of substantially rigid, longitudinally arrayed frame segments 252. The frame may be formed separately and embedded within the body, or may be unitarily formed therewith. In one embodiment, the frame comprises a thickened area of the haptic body. Additionally, the frame and projection may or may not be unitarily constructed. Furthermore, the frame may be of the same material as the plate haptic and/or the lens optic, such as silicone, acrylic, hydrogels, or other similar material.

Figure 2:
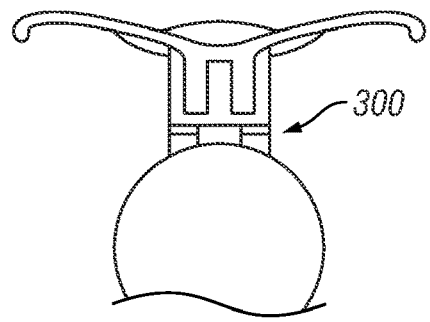
FIG. 2 illustrates a top view of a haptic according to an embodiment of the present invention.

The intraocular lens further comprises at least one connecting member 300, shown in FIGS. 1-4, connecting the plate haptic to the optic. The connecting members are preferably flexible and extend substantially between the plate haptic and the lens optic. The plate haptic is affixed at its proximal end to the connecting member, which is in turn affixed to the lens optic. In one embodiment, the connecting member preferably extends radially from a peripheral edge 110 of the lens optic and is affixed to the proximal end of the plate haptic, as shown in FIGS. 1 and 3. In another embodiment, the connecting member extends substantially longitudinally from the peripheral edge of the lens optic and is affixed to the proximal end of the plate haptic, as shown in FIG. 2.

Figure 4C:
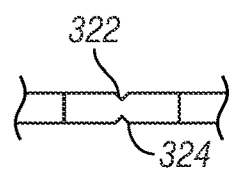
FIG. 4 illustrates a side view of a hinge according to an embodiment of the present invention.
Figure 4A:
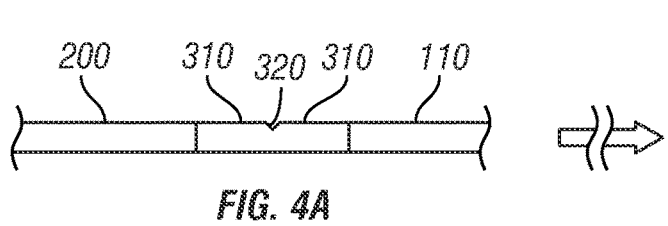
Figure 4B:
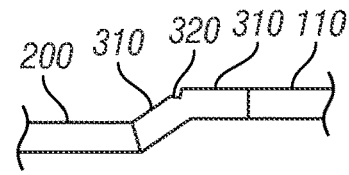

As illustrated in FIG. 1, in one embodiment, the flexible connecting member may comprise at least one strap 310 and a hinge 320 configured to traverse the width of the strap, the strap being flexible about the hinge. In one embodiment, the hinge traverses the strap substantially tangential to the peripheral edge of the lens optic. In another embodiment, the hinge traverses the strap in a substantially lateral direction. The hinge may comprise a groove 320 traversing the strap, as shown in FIG. 4, but multiple grooves may be present without departing from the scope of the invention. As shown in FIG. 4C, in one embodiment, the hinge comprises an upper groove 322 and a lower groove 324 preferably situated on opposing sides of the strap. The hinge thickness may be approximately half the thickness of the strap, or may be, between 0.1 and 0.3 mm.

As illustrated in FIG. 1, in one embodiment, two or more straps couple each of two plate haptics to the optic thereby tending to substantially prevent tilting of the optic with respect to the haptics. In the above embodiment, the straps are preferably removed an equal distance from the longitudinal axis and form an aperture therebetween. In another embodiment, a single strap couples each plate haptic to the optic.

In another embodiment, the connecting member comprises the proximal end of the plate haptic body, the proximal end being substantially thinner than the remainder of the plate haptic body. Preferably, the connecting member is approximately 1 to 1.5 mm long and is thinner than the plate haptic body.

According to one embodiment, when the intraocular lens is implanted into the capsular bag of the eye, the plate haptics and its loops contact the periphery of the capsular bag and operate to support the optic within the eye and to substantially align and fix the lens into the capsular bag, thereby centering the lens optic along the optical axis of the eye. The flexible projections extend beyond the diameter of the capsular bag and the lateral distal plate extensions contact the periphery of the capsular bag, increasing the contact area of the lens within the bag to provide additional fixation and support to for the lens within the capsular bag. In some embodiments, the distal end of the plate haptic comprises a distal flange 240 that engages the capsular bag and further increases the contact area. The distal end of the plates may be either ticker or thinner than the proximal body of the plate haptic.

As illustrated in FIG. 4, the ciliary muscle exerts radial pressure on the ends of the haptics. The longitudinally rigid plate haptics, which naturally vault backwards when placed into the capsular bag, are thus moved centrally and posteriorly towards the optic. Because of the frame, the haptic and its proximal lateral extensions are substantially rigid in the longitudinal direction and they therefore resist bending to the radial force exerted by the ciliary muscle.

The longitudinal length or circumference diameter of the intraocular lens is preferably between 10.0 to 12.0 mm.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that the named inventor believes that the claimed subject matter is what is intended to be patented.

What is claimed is:

1. An intraocular lens for insertion into a capsular bag of an eye, the intraocular lens comprising:
   an optic;
   at least two plate haptics which are coupled to the optic and have a longitudinal axis, wherein each of the at least two plate haptics comprises
      a flexible body having a proximal portion adjacent to said optic and a distal portion remote from said optic, and
      a longitudinally rigid frame having a proximal portion and a distal portion, the proximal portion of the frame being closer to the optic than the distal portion of the frame,
      wherein the longitudinally rigid frame is embedded in and extends substantially the longitudinal length of said flexible body of each of said haptics which substantially reduces the longitudinal flexibility of said haptics while permitting flexibility in a transverse direction; and
   at least one projection extending laterally from the distal portion of the longitudinally rigid frame of at least one of said haptics and operable to engage with the capsular bag;
   wherein a proximal portion of a first one of the at least two plate haptics comprises at least two laterally and proximally extending paddles;
   wherein the longitudinally rigid frame extends into each of the at least two laterally and proximally extending paddles;
   wherein the at least two laterally and proximally extending paddles have ends that are spaced apart wider than the optic; and
   wherein the at least two laterally and proximally extending paddles, in combination, extend proximally to surround a substantial portion, but not all, of the optic.

2. The intraocular lens of claim 1, wherein the rigid frame of each of the at least two plate haptics is operable to restrict deformation of a proximal end of the plate haptic in which the rigid frame is embedded by a force exerted by the ciliary muscle of the eye.

3. The intraocular lens of claim 1, wherein said frame comprises a plurality of substantially rigid, longitudinal frame segments arrayed in said haptics.

4. The intraocular lens of claim 3, wherein the frame further comprises a transverse structure which connects said longitudinal frame segments.

5. The intraocular lens of claim 3, wherein the plurality of substantially rigid, longitudinal frame segments comprises four substantially rigid, longitudinal frame segments.

6. The intraocular lens of claim 1, wherein the rigid frame is substantially comprised of at least one of: polyimide, PMMA, titanium and prolene.

7. The intraocular lens of claim 1, wherein at least one of the haptics comprises proximal edges that are substantially parallel to the longitudinal axis.

8. The intraocular lens of claim 1, wherein the projection is a closed loop.

9. The intraocular lens of claim 1, wherein the projection is an open loop.

10. The intraocular lens of claim 1, wherein the projection is an extension of the distal portion of said frame of at least one of the plate haptics.

11. The intraocular lens of claim 1, wherein the frame is symmetric about the longitudinal axis.

12. The intraocular lens of claim 1, wherein the flexible body and the frame are made from different materials.

13. The intraocular lens of claim 12, wherein the frame is made from at least one of: polyimide, prolene, PMMA and titanium.

14. The intraocular lens of claim 1, wherein each of the haptics is at least as wide as the optic.

15. The intraocular lens of claim 1, wherein each of said at least two laterally and proximally extending paddles is spaced apart laterally from said optic.

16. The intraocular lens of claim 15, wherein each of said at least two laterally and proximally extending paddles, at a most proximal extent, has a free proximal end.

17. The intraocular lens of claim 16, wherein the free proximal ends at the most proximal extent of each of the at least two laterally and proximally extending paddles are unconnected to one another.

18. The intraocular lens of claim 16, wherein the free proximal ends at the most proximal extent of each of the at least two laterally and proximally extending paddles of the first one of the at least two plate haptics are not directly connected to another one of the at least two plate haptics.

19. The intraocular lens of claim 1, wherein said frame extends from a distal portion of one of said haptics into a proximal portion of said one of said haptics.

20. The intraocular lens of claim 1, wherein the at least two laterally and proximally extending paddles, in combination, extend proximally to circumferentially surround a substantial portion, but not all, of the optic.

21. The intraocular lens of claim 1, wherein the longitudinally rigid frame extends from a distal portion of the first one of the plate haptics into a proximal portion of said first one of the plate haptics, adjacent and lateral to the optic.

22. The intraocular lens of claim 1, wherein each of the at least two laterally and proximally extending paddles of the first one of the at least two plate haptics is not directly connected to another one of the at least two plate haptics.

23. An intraocular lens for insertion into a capsular bag of an eye, the intraocular lens comprising:
   an optic;
   at least two plate haptics which are coupled to the optic and have a longitudinal axis, wherein each of the at least two plate haptics comprises
      a flexible body having a proximal portion adjacent to said optic and a distal portion remote from said optic, and
      a longitudinally rigid frame having a proximal portion and a distal portion, the proximal portion of the frame being closer to the optic than the distal portion of the frame,
      wherein the longitudinally rigid frame is embedded in and extends substantially the longitudinal length of said flexible body of each of said haptics which substantially reduces the longitudinal flexibility of said haptics while permitting flexibility in a transverse direction; and
   at least one projection extending laterally from the distal portion of the longitudinally rigid frame of at least one of said haptics and operable to engage with the capsular bag;
   wherein a proximal portion of a first one of the at least two plate haptics comprises at least two laterally and proximally extending paddles;
   wherein the longitudinally rigid frame extends into each of the at least two laterally and proximally extending paddles; and
   wherein the at least one projection is a closed loop.

24. An intraocular lens for insertion into a capsular bag of an eye, the intraocular lens comprising:
   an optic;
   at least two plate haptics which are coupled to the optic and have a longitudinal axis, wherein each of the at least two plate haptics comprises
      a flexible body having a proximal portion adjacent to said optic and a distal portion remote from said optic, and
      a longitudinally rigid frame having a proximal portion and a distal portion, the proximal portion of the frame being closer to the optic than the distal portion of the frame,
      wherein the longitudinally rigid frame is embedded in and extends substantially the longitudinal length of said flexible body of each of said haptics which substantially reduces the longitudinal flexibility of said haptics while permitting flexibility in a transverse direction; and
   at least one projection extending laterally from the distal portion of the longitudinally rigid frame of at least one of said haptics and operable to engage with the capsular bag;
   wherein a proximal portion of a first one of the at least two plate haptics comprises at least two laterally and proximally extending paddles;
   wherein the longitudinally rigid frame extends into each of the at least two laterally and proximally extending paddles; and
   wherein the at least one projection is an open loop.

* * * * *